US006827839B2

(12) United States Patent
Sonnenberg et al.

(10) Patent No.: US 6,827,839 B2
(45) Date of Patent: Dec. 7, 2004

(54) PLATING BATH ANALYSIS

(75) Inventors: Wade Sonnenberg, Upton, MA (US); Mark J. Kapeckas, Marlborough, MA (US); David L. Jacques, Northbridge, MA (US); Raymond Cruz, Waltham, MA (US); Leon R. Barstad, Raynham, MA (US); Elie H. Najjar, Belmont, MA (US); Eugene N. Step, Newton, MA (US); Robert A. Binstead, Marlborough, MA (US)

(73) Assignee: Shipley Company, L.L.C., Marlborough, MA (US)

( * ) Notice: Subject to any disclaimer, the term of this patent is extended or adjusted under 35 U.S.C. 154(b) by 328 days.

(21) Appl. No.: 10/002,039

(22) Filed: Nov. 2, 2001

(65) Prior Publication Data

US 2002/0074244 A1 Jun. 20, 2002

Related U.S. Application Data

(60) Provisional application No. 60/245,311, filed on Nov. 2, 2000.

(51) Int. Cl.$^7$ ............................................... G01N 27/42
(52) U.S. Cl. ....................... 205/775; 205/81; 205/780.5; 205/787; 204/434
(58) Field of Search ............................ 205/775, 780.5, 205/786.5, 787, 794, 81; 204/434

(56) References Cited

U.S. PATENT DOCUMENTS

| 4,038,161 A | * | 7/1977 | Eckles et al. ............... 205/298 |
| 4,132,605 A | | 1/1979 | Tench et al. |
| 4,917,774 A | | 4/1990 | Fisher |
| 5,192,403 A | | 3/1993 | Chang et al. |
| 5,223,118 A | | 6/1993 | Sonnenberg et al. |
| 6,551,479 B1 | * | 4/2003 | Graham et al. ............. 204/434 |

FOREIGN PATENT DOCUMENTS

| DE | 199 11 447 A1 | 3/1999 |
| EP | 0 597 474 A1 | 5/1994 |
| WO | WO 99/57549 | 11/1999 |

* cited by examiner

Primary Examiner—Kaj K. Olsen
(74) Attorney, Agent, or Firm—S. Matthew Cairns

(57) ABSTRACT

Disclosed are methods for determining the quantity of leveler in an electroplating bath in the presence of other organic additives, such as accelerators, brighteners and suppressors. Such methods are fast, work over a broad concentration range of components and can be performed in real-time.

8 Claims, 5 Drawing Sheets

PLATING BATH ANALYSIS

This application claims the benefit of U.S. Provisional Application No. 60/245,311, filed on Nov. 2, 2000.

BACKGROUND OF THE INVENTION

The present invention relates generally to the field of analysis of electroplating baths. In particular, the present invention relates to the analysis of organic additives in electroplating baths.

Electroplating baths for copper and other metals are typically aqueous, or mostly aqueous, solutions composed of metal compounds or salts, ionic electrolytes, and various additives such as brighteners, suppressors, levelers, accelerators, surfactants, defoamers, and the like. These electroplating baths, which are used to deposit metals or semimetals such as copper, nickel, gold, palladium, platinum, ruthenium, rhodium, tin, zinc, antimony, or alloys such as copper-tin (brass), copper-zinc (bronze), tin-lead, nickel-tungsten, cobalt-tungsten-phosphide, and the like are used in applications such as the fabrication of electronic devices and components, such as conductive circuits for printed circuit boards, multichip modules, semiconductor devices and the like.

Reliable operation of these electroplating baths in a manufacturing process requires that methods of analysis are employed to determine the appropriate concentrations of the reagent species for bath startup. These analytical methods are also used to determine the concentrations of species in the bath during operation, often with on-line feedback control, to allow the components of the bath to be monitored and adjusted as required to maintain concentrations within pre-determined limits. Bath analytical methods are also used to determine the chemical identity and concentrations of species that are produced in the bath as a consequence of chemical and electrochemical reactions that take place during bath operation and/or idling.

Electrochemical methods are used principally for the analysis of acid copper plating baths used for plating circuitry on printed wiring boards and integrated circuits. Besides the inorganic components of these plating solutions (copper ions, sulfuric acid and small amounts of chloride ions) the baths contain one or more organic additives (brighteners, suppressors and levelers). In the proper concentrations, these organic additives give a bright, smooth deposit with excellent mechanical and electrical properties.

Analyses of plating bath additives are described by Tench and coworkers in U.S. Pat. No. 4,132,605, and Fisher in U.S. Pat. No. 4,917,774. These methods were devised to measure the brightener concentration in a bath containing a suppressor and inorganic components only. These methods cannot measure the presence of a leveler component in a plating bath containing brightener and suppressor.

The electrochemical methods for plating bath analysis described by Tench et al. and Fisher rely on the fact that the brightener and suppressor work in opposition to one another with respect to their effect on the potential of an object being plated. Suppressors, as their name implies, increase the overpotential for plating and thus suppress the plating rate for any given electrical energy input to the bath. In the presence of suppressors, brighteners lower the plating overpotential and cause the plating rate to increase for any given input of electrical energy to the plating bath. Suppressors cause an abrupt suppression of the plating rate at very low concentrations, on the order of 50 parts per million or less. Above that threshold level the plating overpotential changes very little, if at all. Suppressor concentrations are usually kept in the range of several hundreds to several thousand parts per million to ensure that the suppressor concentration is always well above the threshold value.

U.S. Pat. No. 4,917,774 describes a stepped potential method wherein a three electrode cell is employed. The electrodes are 1) a working electrode, 2) a counter electrode, and 3) a reference electrode which are all immersed in the plating solution to be analyzed. The working electrode is a noble metal such as platinum in the form of a rotating disc. The disc is sealed at one end of a Kel F rod and is rotated during the analysis to ensure that uniform hydrodynamic conditions prevail. The potential of the working electrode is controlled by input from a potentiostat slaved to a computer. For any working potential required, the computer will direct the potentiostat to set the potential difference between the counter electrode and the reference electrode to give the desired potential at the working electrode. The computer and potentiostat can be embodied in a single unit such as the Electroposit™ Bath Analyzer, (Shipley Company, Marlborough, Mass. and S-Systems, Norwood, Mass.). The potential of a working electrode is held at various potentials in a plating solution to clean, equilibrate, plate and strip the plated deposit from the electrode. For example, the cleaning step comprises holding the working electrode at from 1.6 to 2.0 V for from 5 to 30 seconds, the equilibration potential at from 0.5 to 0.6 V for 10 to 60 seconds, the plating potential at from −0.2 to −0.3 V for 1 to 10 seconds, and the stripping potential at 0.2 to 0.3 V for 5 to 30 seconds. A measurement of the initial current flowing during the plating step is directly related to the brightener concentration in the plating solution. When using the Electroposit™ Bath Analyzer, the initial plating current is displayed as Total Brightener Analysis Units ("TBA") units, hereinafter referred to as TBA analysis.

Levelers are often present in plating baths. Like suppressors, levelers cause a reduction of plating rate for any given electrical energy input to the plating bath. Unlike suppressors, whose effect is general in nature, levelers cause a localized depression in plating rate. They act under mass transfer control to suppress the plating rate by adsorbing at locally higher potential regions of the article being plated. The above described electrochemical methods cannot be used when levelers are present in the bath. This is due to the leveler's suppressing effect on the plating rate which varies with its concentration in the bath. To properly analyze for brightener when leveler is present the leveler concentration must already be known. The techniques described above provide no solution for overcoming the confounding effect of the leveler on the brightener, and therefore cannot be used when these two additives coexist in a plating bath.

U.S. Pat. No. 5,223,118 (Sonnenberg et al.) describes an analysis method that measures both brightener and leveler coexisting with suppressor in a plating solution. In this method the brightener concentration is first determined by the TBA method and, if necessary, adjusted by external addition to a value that gives maximum sensitivity for analysis of leveler. The method then uses a freshly prepared copper electrode to monitor the energy input with time to the electrode while plating at an applied current held at a constant value. Such copper electrode is prepared by first plating copper from a separate copper electroplating solution free of organic additive on the electrode. The slope of the resulting energy-time plot is used to quantitatively determine the leveler concentration. However, this method only works with a narrow range of low concentrations of brightener and only within a specific range of leveler concentrations, the analytical procedure is lengthy (ca. 10 minute equilibration period) and is not a real-time analysis. This method measures the plating potential, the slope of which with time is dependent upon the concentration of leveler. Such method has not achieved acceptance in the semiconductor industry.

Other bath analysis methods, such as AC impedance, high pressure liquid chromatography ("HPLC"), ion chromatography ("IC"), titrimetry, gravimetric analysis, optical spectroscopy, and the like have not been widely implemented in commercial bath analysis systems. Titrimetric and gravimetric techniques are more widely used than chromatographic methods, but these methods require the use of various additional chemistries (titrants, complexants, precipitants) and are difficult to implement in an on-line, real-time configuration There is a continuing need for the analysis of brightener and leveler concentration in plating baths, that works over a wide range of brightener concentrations, is simple to perform and does not require the addition of other components to the bath for the procedure to be performed.

SUMMARY OF INVENTION

The present invention overcomes the deficiencies of the conventional analytical methods of cyclic voltammetric stripping ("CVS") and cyclic pulse voltammetric stripping ("CPVS") for the analysis of plating baths containing both leveler and brightener. It has been surprisingly found that the present method provides a simple analytical procedure for determining the quantity of both brightener and leveler in a plating bath, can be performed as a real-time analysis, and can be used with a wide range of brightener concentrations.

The present invention provides a method for determining the quantity of both brightener and leveler in an electroplating bath including the steps of: a) determining the amount of brightener by a method selected from cyclic voltammetric stripping and cyclic pulse voltammetric stripping; b) obtaining a plurality of plating baths where each bath has a known and different quantity of said brightener and leveler, but where the quantity of each in each bath differs from the quantity in the other baths; c) for each bath, providing a counter electrode, a cleaned working electrode and a reference electrode immersed in said bath, and carrying out a predetermined sequence of steps including: 1. cleaning and oxidizing the surface of the working electrode at a fixed potential for a period of time; 2. equilibrating said working electrode to absorb brightener according to a step selected from equilibrating without energy input for a time until the change in energy output with time is minimal or equilibrating for a set time at a fixed potential; 3. plating metal ions on said working electrode with energy input for a time sufficient to measure initial plating energy output; and 4. optionally continuing to plate metal ions for a time sufficient to measure the change in energy output with time; 5. stripping at a potential and for a period of time sufficient to remove the metal ions plated in steps 3 and 4; d) for each bath, correlating the quantity of leveler with the energy output value obtained in step 3 or 4; e) obtaining a plating bath having an unknown quantity of brightener and leveler, placing said electrodes in said bath and performing said predetermined sequence of steps; f) choosing from said correlations in step d), a particular correlation for a bath containing substantially the amount of brightener determined in step a); and g) choosing from the particular correlation in step f), a quantity of leveler which corresponds to said energy outputs recorded for said bath with the unknown quantity of brightener and leveler.

The present invention also provides a method for determining the quantity of both brightener and leveler in an electroplating bath including the steps of: a) obtaining a plurality of plating baths, where each bath has a known and different quantity of said brightener and leveler, but where the quantity of each in each bath differs from the quantity in the other baths; b) sweeping for each of said baths an inert, working electrode at a predetermined rate through a plurality of voltammetric cycles until a condition of steady state is obtained, each of said voltammetric cycles including a metal plating range and a metal stripping range for each of said baths of said plurality of baths, each of said voltammetric cycles comprising a sweeping of a voltage toward one polarity followed by a sweeping of said voltage toward a reverse of said one polarity to complete said cycle; c) measuring the coulombs utilized during said metal stripping range of said cycle for each of said baths of said plurality of baths, whereby a correlation is obtained between the effective quantity of brightener and said coulombs utilized during said metal stripping range; d) obtaining a bath having an unknown quantity of both brightener and leveler; e) sweeping for said unknown bath an inert, working electrode at said predetermined rate through a plurality of voltammetric cycles until a condition of steady state is obtained, each of said voltammetric cycles including a metal plating range and a metal stripping range for said bath having an unknown quantity of brightener, each of said voltammetric cycles comprising a sweeping of a voltage toward one polarity followed by a sweeping of said voltage toward a reverse of said one polarity to complete said cycle; f) measuring the coulombs utilized during said metal stripping range of said cycle for said bath having an unknown quantity of brightener; g) choosing from said correlation a quantity of brightener which corresponds to said coulombs utilized for said bath having an unknown quantity of organic leveling agent; h) for each of said plurality of plating baths in step a), providing a counter electrode, a cleaned working electrode and a reference electrode immersed in said bath, and carrying out a predetermined sequence of steps including: 1. cleaning and oxidizing the surface of the working electrode at a fixed potential for a period of time; 2. equilibrating said working electrode to absorb brightener according to a step selected from equilibrating without energy input for a time until the change in energy output with time is minimal or equilibrating for a set time at a fixed potential; 3. plating metal ions on said working electrode with energy input for a time sufficient to measure initial plating energy output; and 4. optionally continuing to plate metal ions for a time sufficient to measure the change in energy output with time; 5. stripping at a potential and for a period of time sufficient to remove the metal ions plated in steps 3 and 4; i) for each bath, correlating the quantity of leveler with the energy output value obtained in step 3 or 4; j) obtaining a plating bath having an unknown quantity of brightener and leveler, placing said electrodes in said bath and performing said predetermined sequence of steps; k) choosing from said correlations in step i), a particular correlation for a bath containing substantially the amount of brightener determined in step g); and 1) choosing from the particular correlation in step k), a quantity of leveler which corresponds to said energy outputs recorded for said bath with the unknown quantity of brightener and leveler.

The present invention further provides a method for determining the quantity of leveler in an electroplating bath including the steps of: a) obtaining a plurality of plating baths where each bath has a known and different quantity of brightener and leveler, wherein the quantity of leveler in each bath differs from the quantity in the other baths; b) for each bath, providing a counter electrode, a cleaned working electrode and a reference electrode immersed in said bath, and carrying out a predetermined sequence of steps including: 1. cleaning and oxidizing the surface of the working electrode at a fixed potential for a period of time; 2. equilibrating said working electrode to absorb brightener according to a step selected from equilibrating without energy input for a time until the change in energy output with time is minimal or equilibrating for a set time at a fixed potential; 3. plating metal ions on said working electrode with energy input for a time sufficient to measure initial plating energy output; and 4. optionally continuing to plate metal ions for a time sufficient to measure the change in energy output with time; 5. stripping at a potential and for a period of time sufficient to remove the metal ions plated in steps 3 and 4; c) for each bath, correlating the quantity of leveler with the energy output value obtained in step 3 or 4; d) obtaining a plating bath having an unknown quantity of leveler; e) diluting the bath having an unknown quantity of leveler with a fixed concentration of brightener and placing said electrodes in said bath and performing said predetermined sequence of steps; f) choosing from said correlation in step c), a quantity of leveler which corresponds to said energy outputs recorded for said bath with the unknown quantity of leveler.

DETAILED DESCRIPTION OF THE INVENTION

Figure 1:
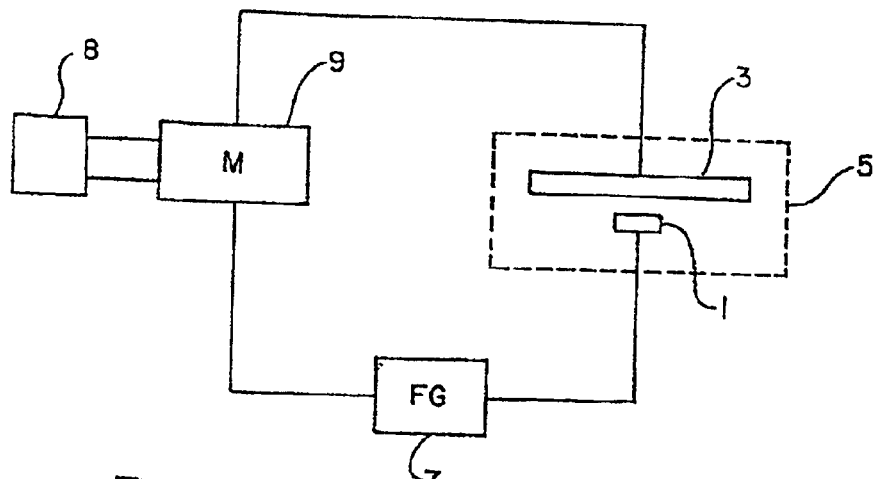
FIG. 1 is a schematic wiring diagram of a device according to an embodiment of the invention.

The following abbreviations shall have the following meanings unless the text clearly indicates otherwise: CVS= cyclic voltammetric stripping; CPVS=cyclic pulse voltammetric stripping; ° C.=degrees Centigrade; g/L=grams per liter; cm=centimeter; mA=milliamperes; $mA/cm^2$= milliamperes per square centimeter; mL=milliliter; mL/L= milliliters per liter; V=volts; and ppm=parts per million.

As used throughout this specification, the term "plating" refers to metal electroplating, unless the context clearly indicates otherwise. "Deposition" and "plating" are used interchangeably throughout this specification. "Halo" refers to fluoro, chloro, bromo, and iodo. Likewise, "halide" refers to fluoride, chloride, bromide and iodide. "Alkyl" includes straight chain, branched and cyclic alkyl groups. "Brightener" refers to an organic additive that increases the plating rate of the electroplating bath. The terms "brightener" and "accelerator" are used interchangeably throughout this specification. "Leveler" refers to an organic compound that is capable of providing a substantially planar metal layer. "Energy output" refers generally to any energy output and includes energy flow, energy throughput, cell current and plating current. "Energy input" refers generally to any energy input and includes potential energy, cell potential, electrode potential and reductive potential.

All percentages and ratios are by weight unless otherwise indicated. All ranges are inclusive and combinable.

The subject invention provides a novel method for determining the quantity of brighteners and levelers coexisting in a plating solution. The present method provides for direct analysis of the quantity of leveler without the need for determining the ratio of brightener to leveler in a plating solution. Also, the present method provides a method for determining the quantities of both brightener and leveler that is more accurate than prior methods. The present invention is useful over a broader range of concentrations of both brightener and leveler than known methods, e.g. the method of Sonnenberg et al.

The present invention provides a method for determining the quantity of both brightener and leveler in an electroplating bath including the steps of: a) determining the amount of brightener by a method selected from cyclic voltammetric stripping and cyclic pulse voltammetric stripping; b) obtaining a plurality of plating baths where each bath has a known and different quantity of said brightener and leveler, but where the quantity of each in each bath differs from the quantity in the other baths; c) for each bath, providing a counter electrode, a cleaned working electrode and a reference electrode immersed in said bath, and carrying out a predetermined sequence of steps including: 1. cleaning and oxidizing the surface of the working electrode at a fixed potential for a period of time; 2. equilibrating said working electrode to absorb brightener according to a step selected from equilibrating without energy input for a time until the change in energy output with time is minimal or equilibrating for a set time at a fixed potential; 3. plating metal ions on said working electrode with energy input for a time sufficient to measure initial plating energy output; and 4. optionally continuing to plate metal ions for a time sufficient to measure the change in energy output with time; 5. stripping at a potential and for a period of time sufficient to remove the metal ions plated in steps 3 and 4; d) for each bath, correlating the quantity of leveler with the energy output value obtained in step 3 or 4; e) obtaining a plating bath having an unknown quantity of brightener and leveler, placing said electrodes in said bath and performing said predetermined sequence of steps; f) choosing from said correlations in step d), a particular correlation for a bath containing substantially the amount of brightener determined in step a); and g) choosing from the particular correlation in step f), a quantity of leveler which corresponds to said energy outputs recorded for said bath with the unknown quantity of brightener and leveler.

A wide variety of electroplating baths may be analyzed according to the present invention to determine the quantity of leveler in the presence of brightener. Suitable electroplating baths include, but are not limited to, copper, nickel, chromium, zinc, tin, lead, gold, silver, and cadmium electroplating baths, and preferably copper electroplating baths.

Working electrodes include any that provide a uniform current density and controlled agitation. Suitable working electrodes include, but are not limited to, platinum, copper, nickel, chromium, zinc, tin, gold, silver, lead, cadmium, solder, glassy carbon, mercury and stainless steel. Preferably, the working electrode is a noble metal, more preferably platinum or gold, and even more preferably platinum. The working electrode typically has a flat, polished surface, small diameter and may be mounted flush with the end of a Kel-F cylinder. To establish relative motion between the working electrode and the bath, a motor is typically used to rotate the working electrode to which contact is made by slip brushes. Thus, it is further preferred that the working electrode is a rotating disk electrode ("RDE"). A small diameter disk is preferred since a larger diameter will result in poor sensitivity due to non-uniform current density across the diameter. The working electrode used in the brightener quantitative determination step and in the leveler quantitative determination step may be the same or different. Preferably both are platinum. The reference electrode is conventionally, a saturated Calomel reference electrode ("SCE"). The counter electrode may be an noble metal or noble metal alloy such as gold, platinum, platinum-ruthenium and the like, or may be a soluble anode composed of the same metal that is present in the electrolyte bath such as a soluble copper anode for use with a copper electrolyte bath.

Typically, the first step of the present invention is to determine the quantity of brightener in a plating bath sample. Such brightener determination is performed using either cyclic voltammetric stripping and cyclic pulse voltammetric stripping methods. In such methods a working noble metal rotating disc electrode immersed in a plating solution is either scanned or stepped over a range of potentials to clean, equilibrate, plate and strip the deposit from the electrode. In the case where the working electrode is scanned (hereafter called CVS), the quantity of brightener in solution is related to the number of coulombs passed during stripping of the deposit from the electrode. In the case where the working electrode is stepped through a range of potentials (hereafter called CPVS), the initial current flowing during the plating step is related to the quantity of brightener in the solution.

Such CVS and CPVS methods are well known in the art. A variety of instruments are commercially available to perform these analyses utilizing such methods and incorporate a variety of steps. Such instruments are widely used in the printed wiring board industry for control of certain electroplating baths. Suitable commercial instruments are those sold by ECI Technology, Inc. (East Rutherford, N.J.).

Exemplary CVS or CPVS analytical methods are those disclosed in U.S. Pat. 4,132,605 (Tench et al.) and Tench et al., *Pulse Voltammetric Stripping Analysis of Acid Copper Plating Baths*, J. Electrochem. Soc., April 1985, pp 831–834, both herein incorporated by reference. In such methods, a small amount of metal is electrodeposited onto an inert electrode (e.g., platinum or gold) under controlled conditions of electrode potential and mass-transport in the solution. The amount of metal deposited is determined by integrating the current peak arising from re-dissolution or "stripping" of the deposited metal from the surface as the electrode potential is swept anodic at a known rate. The quantity of metal deposited, and subsequently re-dissolved, is related to the concentration of brightener affecting the rate of deposition. The cathodic current required to deposit the metal is also an indication of the deposition rate, but it is intrinsically less precise because of other reduction reactions (such as the reduction of organic compounds in the bath or water to hydrogen) occurring during the cathodic portion of the voltammetric cycle.

FIG. 1 is a schematic wiring diagram showing a device for determining the quantity of brightener according to the present invention. A working electrode 1 and a counter electrode 3 are immersed in a bath in cell 5. The counter electrode is selected and designed so as not to be easily polarized in the particular bath being evaluated. This is accomplished, in part, by making the counter electrode large relative to the working electrode and by placing it close to the working electrode.

A function generator 7 sweeps the working electrode 1 through a voltage versus time cycle at a specific rate while a coulometer 9 measures the coulombs (amp-seconds) flowing between the counter electrode 3 and the working electrode 1 during the metal stripping portion of the voltammetric cycle. The coulometer may be an ammeter whose output can be fed into a recorder for determining the coulombs utilized during the stripping portion of the cycle, or the output can go directly into a microprocessor or computer 8 for direct correlation and comparison of the coulombs utilized.

Figure 2:
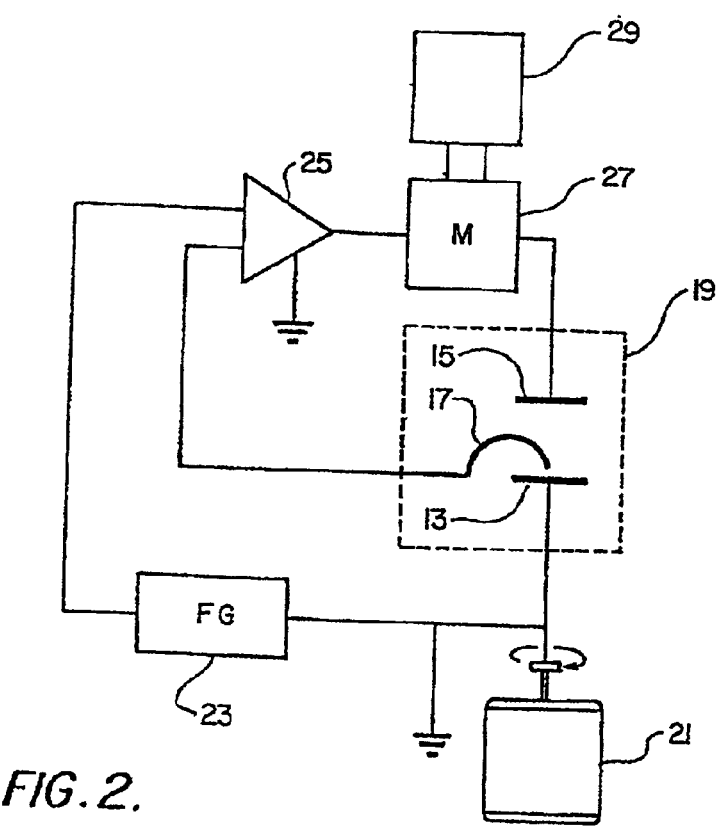
FIG. 2 is a schematic wiring diagram of a device according to another embodiment of the invention.

FIG. 2 shows the schematic wiring diagram for a more elaborate device for determining the quantity of brightener. Three electrodes, a working electrode 13, a counter electrode 15, and a reference electrode 17, are immersed in a bath in cell 19. To establish relative motion between the working electrode 13 and the bath, a motor 21 is used to rotate the working electrode 13 to which contact is made by slip brushes.

In one embodiment, the working electrode 13 is platinum and the counter electrode 15 is platinum—10% rhodium, although any conductive material, such as gold, which is inert in the particular bath, can be used. The rotatable working electrode 13 has a flat, polished surface, 0.13 cm$^2$ in area, mounted flush with the end of a 1.27 cm diameter Kel-F cylinder. The reference electrode 17 is, conveniently, a saturated calomel reference electrode ("SCE"). A function generator 23 and an electronic potentiostat 25 are used to control the potential relative to the reference electrode 17. A digital coulometer 27 measures the coulombs flowing during the stripping portion of the voltammetric cycle.

A microprocessor or computer 29 can be coupled to the digital coulometer to compare the measured coulombs with a previously established correlation. The microprocessor or computer 8, 29, shown in FIGS. 1 and 2, can be coupled to the circuit so that they are triggered either manually or by a suitable signal from the function generator 7, 23, or from the working electrode 1, 13.

To achieve maximum sensitivity, there must be sufficient relative motion between the working electrode and the bath to maintain a uniform supply of plating ingredients at the electrode surface. Without such motion, the bath becomes depleted at the surface and the deposition rate obtained does not reflect to correct rate for the bulk solution. In the embodiment shown in FIG. 2, the working electrode 13 is rotated by motor 21 to obtain controlled relative motion between it and the plating bath. Other means of obtaining relative motion can be used, such as a pump for moving the bath across the face of the electrode.

According to the present method, voltammetric cycles are first run under controlled conditions of electrode potential and mass-transport in the solution for baths of known quantity, or of known concentration of additives, to obtain the current or coulombs during the stripping range of the cycle. The quantity or concentration is then correlated with the peak stripping current or with the stripping coulombs to obtain the concentration as a function of the peak stripping current or of the stripping coulombs.

In some cases, significant variations in the stripping current are observed from day to day for a particular bath composition and are probably caused by uncontrolled variables, such as changes in the working electrode surface. Such variations can be mitigated by measuring the stripping current utilized by a fixed standard immediately before or after making the desired measurement and then utilizing the ratio of the two measurements to obtain the correlation between stripping current and concentration of ingredients.

In a further embodiment of the invention, variations in stripping current caused by uncontrolled variables are mitigated by using an internal standard provided by a static working electrode in the same bath. When there is no relative motion between the bath and the surface of the working electrode, the concentration of the additives (brightener) at the surface decreases with continued potential cycling until a steady state level is established. The level established is determined by the rate of diffusion of the additive in the bath.

In the present method, the quantity of brightener in an electroplating bath can be determined according to the steps of: a) obtaining a plurality of plating baths, where each bath has a known and different quantity of said brightener and leveler, but where the quantity of each in each bath differs from the quantity in the other baths; b) sweeping for each of said baths an inert, working electrode at a predetermined rate through a plurality of voltammetric cycles until a condition of steady state is obtained, each of said voltammetric cycles including a metal plating range and a metal stripping range for each of said baths of said plurality of baths, each of said voltammetric cycles comprising a sweeping of a voltage toward one polarity followed by a sweeping of said voltage toward a reverse of said one polarity to complete said cycle; c) measuring the coulombs utilized during said metal stripping range of said cycle for each of said baths of said plurality of baths, whereby a correlation is obtained between the effective quantity of brightener and said coulombs utilized during said metal stripping range; d) obtaining a bath having an unknown quantity of both brightener and leveler; e) sweeping for said unknown bath an inert, working electrode at said predetermined rate through a plurality of voltammetric cycles until a condition of steady state is obtained, each of said voltammetric cycles including a metal plating range and a metal stripping range for said bath having an unknown quantity of brightener, each of said voltammetric cycles comprising a sweeping of a voltage toward one polarity followed by a sweeping of said voltage toward a reverse of said one polarity to complete said cycle; f) measuring the coulombs utilized during said metal stripping range of said cycle for said bath having an unknown quantity of brightener; and g) choosing from said correlation a quantity of brightener which corresponds to said coulombs utilized for said bath having an unknown quantity of organic leveling agent.

Thus, in another embodiment, the present invention provides a method for determining the quantity of both brightener and leveler in an electroplating bath including the steps of: a) obtaining a plurality of plating baths, where each bath has a known and different quantity of said brightener and leveler, but where the quantity of each in each bath differs from the quantity in the other baths; b) sweeping for each of said baths an inert, working electrode at a predetermined rate through a plurality of voltammetric cycles until a condition of steady state is obtained, each of said voltammetric cycles including a metal plating range and a metal stripping range for each of said baths of said plurality of baths, each of said voltammetric cycles comprising a sweeping of a voltage toward one polarity followed by a sweeping of said voltage toward a reverse of said one polarity to complete said cycle; c) measuring the coulombs utilized during said metal stripping range of said cycle for each of said baths of said plurality of baths, whereby a correlation is obtained between the effective quantity of brightener and said coulombs utilized during said metal stripping range; d) obtaining a bath having an unknown quantity of both brightener and leveler; e) sweeping for said unknown bath an inert, working electrode at said predetermined rate through a plurality of voltammetric cycles until a condition of steady state is obtained, each of said voltammetric cycles including a metal plating range and a metal stripping range for said bath having an unknown quantity of brightener, each of said voltammetric cycles comprising a sweeping of a voltage toward one polarity followed by a sweeping of said voltage toward a reverse of said one polarity to complete said cycle; f) measuring the coulombs utilized during said metal stripping range of said cycle for said bath having an unknown quantity of brightener; g) choosing from said correlation a quantity of brightener which corresponds to said coulombs utilized for said bath having an unknown quantity of organic leveling agent; h) for each of said plurality of plating baths in step a), providing a counter electrode, a cleaned working electrode and a reference electrode immersed in said bath, and carrying out a predetermined sequence of steps including: 1. cleaning and oxidizing the surface of the working electrode at a fixed potential for a period of time; 2. equilibrating said working electrode to absorb brightener according to a step selected from equilibrating without energy input for a time until the change in energy output with time is minimal or equilibrating for a set time at a fixed potential; 3. plating metal ions on said working electrode with energy input for a time sufficient to measure initial plating energy output; and 4. optionally continuing to plate metal ions for a time sufficient to measure the change in energy output with time; 5. stripping at a potential and for a period of time sufficient to remove the metal ions plated in steps 3 and 4; i) for each bath, correlating the quantity of leveler with the energy output value obtained in step 3 or 4; j) obtaining a plating bath having an unknown quantity of brightener and leveler, placing said electrodes in said bath and performing said predetermined sequence of steps; k) choosing from said correlations in step i), a particular correlation for a bath containing substantially the amount of brightener determined in step g); and l) choosing from the particular correlation in step k), a quantity of leveler which corresponds to said energy outputs recorded for said bath with the unknown quantity of brightener and leveler.

Figure 3:
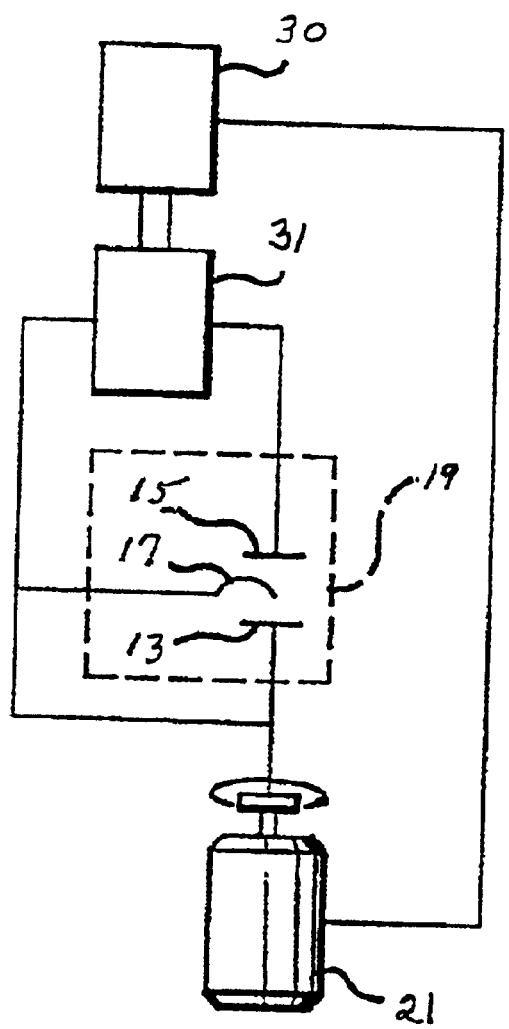
FIG. 3 is a schematic wiring diagram of a device according to a third embodiment of the invention.

FIG. 3, is a schematic wiring diagram showing a device suitable for the determination of quantity of leveler according to the present invention. Three electrodes, a working electrode 13, a counter electrode 15, and a reference electrode 17, are immersed in a bath in cell 19. To establish relative motion between the working electrode 13 and the bath, a motor 21 is used to rotate the working electrode 13 to which contact is made by slip brushes. A computer 30 is used to control an electronic potentiostat 31 which controls the energy input between the working electrode and counter electrode relative to the reference electrode. Using a suitable program, the energy input sequences of the present invention may be applied to the working electrode. The output of the device can also be plotted on a recorder to graphically display the changes in energy output versus time for each step. The terms "energy input" and "energy output" in the following description of the methods and claims will refer to control of the potential (energy input) while monitoring current density (energy output), or control of current density (energy input) while monitoring potential (energy output).

The following description of the method will be described by reference to energy input as current and energy output as potential, and will be described by reference to standard acid/copper electroplating baths. It is possible however to use the method to control other metal electroplating baths such as nickel, chromium, zinc, tin, gold, silver, lead, cadmium and solder. The working electrode is normally selected or initially plated to match the metal in the plating bath in order to maximize adsorption of the respective brighteners used in the baths.

While the present invention may be used with a wide variety of plating baths, it will be illustrated with respect to a copper electroplating bath. A typical copper electroplating solution useful for the practice of this invention has a composition as follows:

| Component | Amount |
| --- | --- |
| Copper ions | 2.5 to 40.0 g/l |
| Sulfuric acid (added) | 0 to 450 g/l |
| Chloride ions | 20 to 100 ppm |
| Organic additive | As required |
| Water | To 1 liter |

The plating solutions are used in the conventional manner, with operating temperatures preferably between 10° and 30° C., and controlled solution agitation.

The method of determining the quantity of leveler typically begins with a cleaning step to clean the working electrode. The working electrode is typically cleaned chemically by treating with nitric acid followed by rinsing with deionized water. The chemically cleaned working electrode is immersed in the bath to be analyzed along with a counter electrode. Once immersed in the bath, the working electrode is then cleaned and oxidized at a fixed potential for a period of time. Such potentiometric cleaning may be carried out at approximately 80 mA/cm$^2$ for a time sufficient to clean the electrode or until the voltage reaches 1.6 volts. Alternatively, the cleaning may be carried out at 1.6 volts for a period of time such as up to 10 seconds. The oxidation of the working electrode is critical to the analysis to be performed, particularly with a platinum RDE.

Optionally, the second step is to plate a thin layer of copper, approximately 5 to 500 microinches, on the disk by placing the disk in an electroplating bath solution for 10 to 300 seconds at a plating current of from 1 to 100 mA/cm$^2$. The solution may be a standard solution containing only the inorganic chemicals or an actual bath. The use of this thin film of copper eliminates problems associated with nucleation of metal on the disk during analysis. If the disk is made of a metal which readily adsorbs organic additives, or induces potential driven adsorption of the additives, used in electroplating baths, this step is not needed.

In the next step, the bath sample may be substituted for the standard solution containing only the inorganic chemicals, if not used in the initial plating step, with controlled agitation. Brighteners and levelers used in conjunction with the present invention include any sulfonated sulfur-containing compounds which are known and used in the electroplating art. Suitable brighteners useful in the practice of the invention contain the group S—R$_1$—S, where R$_1$ may be an alkyl or aryl group, and are illustrated by the following structural formulas: HO$_3$S—R$_2$—SH, HO$_3$S—R$^2$—S—S—R$_2$—SO$_3$H (where R$_2$=C$_1$-C$_6$ alkyl) and HO$_3$S—Ar—S—S—Ar—SO$_3$H (where Ar=phenyl or naphthyl). Typical of such compounds are those disclosed in U.S. Pat. Nos. 3,770,598, 4,374,709, 4,376,685, 4,555,315 and 4,673,469, all incorporated herein by reference.

Levelers that may be added to the bath included those which contain a N—R$_1$—S group, where R$_1$ may be an alkyl or aryl group, and are illustrated by compounds disclosed in U.S. Pat. Nos. 4,376,685, 4,555,315, and 3,770,598, all incorporated herein by reference. Other suitable levelers include reaction products of amines such as imidazole with epoxides such as epichlorohydrin.

In addition to the organic components identified above, as is known in the art, other organic additives may be used in the plating solution such as surfactants, wetting agents and carriers.

The electrode may be equilibrated by not applying current to the electrodes (open circuit potential or "OCP") and allowing the disk electrode to adsorb brightener for a period of time typically ranging between 5 seconds to 20 minutes, or until the equilibration potential becomes stable (i.e. change in potential with time is minimal). Alternatively, the electrode may be equilibrated for a set time such as up to 60 seconds at a fixed potential. Typically, the fixed potential is within 0.2 V of the OCP, and preferably within 0.1 V of the OCP. For example, when the working electrode is a platinum electrode and the electroplating bath is a copper electroplating bath, a suitable fixed potential for the equilibration step is 0.4 to 0.7 V, and preferably 0.5 to 0.6 V. It is important that the brightener concentration remain unchanged during analysis, by having sufficient volume present, and that temperature and agitation are controlled throughout the equilibration process. For example, when using a 0.4 cm (0.156 inch) diameter disk, a minimum of 100 mL sample would be a sufficient volume. At the end of this equilibration step, the level of brightener may be correlated to the final value of the potential, but such correlation is not required.

In the next step, copper plating is initiated by plating at a current density from 1 to 100 mA/cm$^2$ for 0.001 second to 60 seconds. During this time, copper ions are deposited on the electrode. These ions may be combined with or bound to leveler, brightener, chloride ions, water and/or wetting agents present in the bath. The initial potential reading, upon initiation of plating, is directly related to the leveler concentration. The initial potential may be correlated to the concentration of leveler.

The slope of the potential-time plot to be determined in the next step is a function of the ratio of brightener to leveler and the slopes may vary depending on the absolute concentration of brightener. Once the quantity of brightener is determined from the previous steps (CVS or CPVS), it may be necessary to add additional brightener to the sample so that the amount of brightener more closely approximates the actual value of brightener in the standards. Once this is done, the ratio of brightener to leveler will more accurately reflect the absolute amount of leveler.

Optionally, the plating may be continued for a period of time to measure the change in energy output with time. As the plating process continues, changes in energy output can also be correlated to the concentration of leveler. This step of continued plating may for a period of time ranging between 1 second to 10 minutes. The slope of plots of changes in energy output over time for various standard concentrations of leveler when the brightener is held constant can be correlated to the ratio of brightener to leveler in the bath, and is used to determine quantity of leveler present in the bath.

After the metal ions have been plated or deposited, they must be stripped or removed from the electrode. Such stripping is at a potential and for a period of time sufficient to substantially remove and preferably remove the metal ions deposited during the initial and optionally continued plating steps. The stripping may be done at a fixed potential or the potential may be swept. The period of time of such stripping is dependent upon the thickness of the metal deposited. The potential at which such metal is stripped is dependent upon the particular metal deposited. For example, when the deposit is copper, it is typically stripped at a potential of +0.2 V for 5 seconds.

In another embodiment, the quantity of leveler in an electroplating bath may be determined without the use of CVS or CPVS to determine the quantity of brightener. In this embodiment, a plurality of plating baths where each bath has a known and different quantity of brightener and leveler, wherein the quantity of leveler in each bath differs from the quantity in the other baths are prepared to provide a standard curve. The quantity of brightener in each bath is the same, only the quantity of leveler varies.

In the first step of this alternative procedure, a counter electrode, a cleaned working electrode and a reference electrode are immersed in each bath, and a predetermined sequence of steps are performed, the steps including: 1. cleaning and oxidizing the surface of the working electrode at a fixed potential for a period of time; 2. equilibrating said working electrode to absorb brightener according to a step selected from equilibrating without energy input for a time until the change in energy output with time is minimal and equilibrating for a set time at a fixed potential; 3. plating metal ions on said working electrode with energy input for a time sufficient to measure initial plating energy output; and 4. optionally continuing to plate metal ions for a time sufficient to measure the change in energy output with time. These are the same sequence of steps as described above. The quantity of leveler is correlated the with the energy output value obtained in step 3 or 4. This provides a standard curve rather than the usual family of curves that are obtained by the methods described above.

A plating bath having an unknown quantity of leveler is diluted with a leveler-free composition including a fixed concentration of brightener. The fixed concentration of brightener is that concentration of brightener used in the plating bath. Preferably, the leveler-free composition further includes the same components used in the plating bath being analyzed, except that level is not present. Thus, it is further preferred that the leveler-free composition include the same metal as in the electroplating bath and suppressor. Preferably, the sample the of bath having an unknown quantity of leveler is diluted 5 to 1, and more preferably 10 to 1 with the leveler-free composition. The electrodes are placed in the bath to be analyzed and the above predetermined sequence of steps are performed. The energy output recorded is then compared to the calibration curve (correlation) to quantity of leveler.

Thus, the present invention further provides a method for determining the quantity of leveler in an electroplating bath comprising the steps of: a) obtaining a plurality of plating baths where each bath has a known and different quantity of brightener and leveler, wherein the quantity of leveler in each bath differs from the quantity in the other baths; b) for each bath, providing a counter electrode, a cleaned working electrode and a reference electrode immersed in said bath, and carrying out a predetermined sequence of steps comprising: 1. cleaning and oxidizing the surface of the working electrode at a fixed potential for a period of time; 2. equilibrating said working electrode to absorb brightener according to a step selected from equilibrating without energy input for a time until the change in energy output with time is minimal and equilibrating for a set time at a fixed potential; 3. plating metal ions on said working electrode with energy input for a time sufficient to measure initial plating energy output; and 4. optionally continuing to plate metal ions for a time sufficient to measure the change in energy output with time; 5. stripping at a potential and for a period of time sufficient to remove the metal ions plated in steps 3 and 4; c) for each bath, correlating the quantity of leveler with the energy output value obtained in step 3 or 4; d) obtaining a plating bath having an unknown quantity of leveler; e) diluting the bath having an unknown quantity of leveler with a leveler-free composition comprising a fixed concentration of brightener and placing said electrodes in said bath and performing said predetermined sequence of steps; f) choosing from said correlation in step c), a quantity of leveler which corresponds to said energy outputs recorded for said bath with the unknown quantity of leveler. It is preferred that this method be used when the leveler is a reaction product of an amine with an epoxide and particularly with a reaction product of imidazole with epichlorohydrin.

The above methods may be performed at a range of temperatures. The analysis of the bath containing the unknown amount of leveler should be performed at the same temperature as the calibration curve samples or family of calibration curve samples. A concentration of brightener of 2 ppm or greater suffices to provide sufficient accuracy for analysis of the leveler. When the quantity of leveler is determined without first determining brightener concentration by CVS or CPVS, it is preferred that the brightener concentration is from 20 to 25 ppm.

The following examples are presented to illustrate further various aspects of the present invention, but are not intended to limit the scope of the invention in any aspect.

EXAMPLE 1

Figure 4:
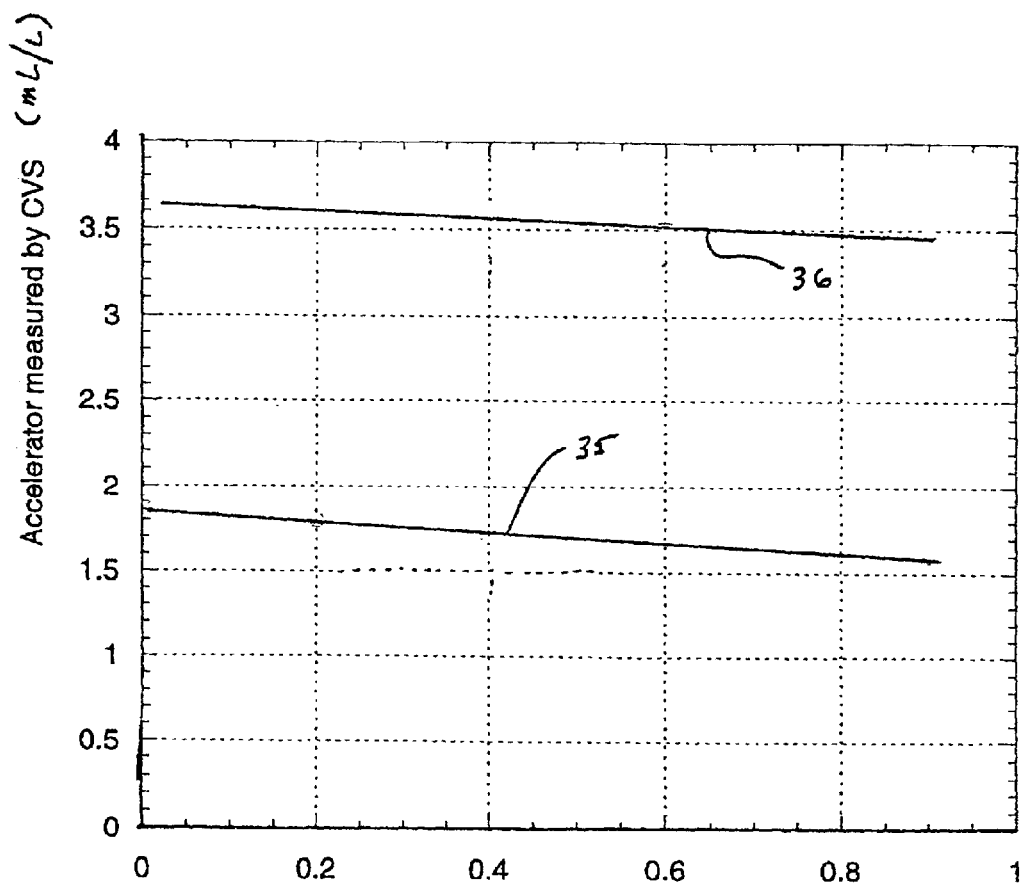
FIG. 4 is a curve showing the correlation showing the effect of leveler concentration on the amount of accelerator as measured by CVS.

A series of copper electroplating baths was prepared by combining 70 g/L copper sulfate pentahydrate, 175 g/L sulfuric acid, 20–75 ppm of chloride ion, and 25 mL/L of polymeric suppressor. To each bath was added either 2 or 4 mL/L of accelerator (brightener). To each bath was added a known amount of leveler X of up to 1 m/L. The suppressor, accelerator and leveler used were obtained from Shipley Company. The accelerator had a general formula that met the criteria of S—$R_1$—S and leveler X had a general formula of N—$R_1$C—S, as defined above. Each bath was analyzed for the quantity of accelerator by CVS using a standard analytical program and a commercially available instrument from ECI technology, Inc. FIG. 4 is a plot showing the affect of the concentration of leveler X on the determination of accelerator concentration by CVS. Line 35 shows the affect of leveler X on baths containing 2 ML/L of accelerator and Line 36 shows the affect of leveler X on baths containing 4 mL/L of accelerator. From these data, it can be seen that the determination of accelerator concentration by CVS is independent of the leveler concentration. Thus, CVS is a suitable method for determining the quantity of accelerator in an electroplating bath containing leveler.

EXAMPLE 2

A series of copper electroplating baths was prepared by combining 80 g/L copper sulfate pentahydrate, 225 g/L sulfuric acid, 20–75 ppm of chloride ion, 25 mL/L of polymeric suppressor and 2 mL/L of accelerator. To each bath was added a known amount of leveler X. The suppressor, accelerator and leveler are those described in Example 1. Each bath was analyzed for the quantity of accelerator by CVS using a standard analytical program and a commercially available instrument from ECI technology, Inc. Each bath was also analyzed for the concentration of accelerator (TBA analysis) using a standard program on an Electroposit Bath Analyzed available from S-Systems, Norwood, Mass. The results are reported in Table 1. The amount of accelerator by TBA is reported in TBA units.

TABLE 1

| Leveler X (mL/L) | Accelerator (mL/L) by CVS | Accelerator Amount in TBA Units |
|---|---|---|
| 0 | 1.83 | 21.8 |
| 0.05 | 1.83 | 18.9 |
| 0.1 | 1.9 | 15.9 |
| 0.2 | 1.73 | 11.3 |
| 0.3 | 1.73 | 9.0 |
| 0.4 | 1.73 | 7.45 |
| 0.5 | 1.70 | 6.6 |
| 0.6 | 1.77 | 5.6 |

From these data, it can be seen that accelerator analysis by CVS is independent of leveler concentration.

EXAMPLE 3

Three copper electroplating baths were prepared by combining 80 g/L copper sulfate pentahydrate, 225 g/L sulfuric acid, 20–75 ppm of chloride ion, 5 mL/L of polymeric suppressor, 1 m/L of the accelerator of Example 1 and up to 12.5 mL/L of leveler Y. Leveler Y which was a reaction product of a heterocyclic amine with epichlorohydrin. These baths were analyzed using the CVS method of Example 1. The results are reported in Table 2.

TABLE 2

| Leveler Y (mL/L) | Accelerator (mL/L) by CVS |
|---|---|
| 0 | 0.97 |
| 5.0 | 0.93 |
| 12.5 | 0.90 |

The above data clearly shows that accelerator determination by CVS is independent of leveler concentration.

EXAMPLE 4

A series of copper electroplating baths was prepared according to Example 3 except that 2 mL/L of the accelerator of Example 1 and up to 6 mL/L of leveler Y were used. These baths were analyzed using the TBA method of Example 2. The results are reported in Table 3.

TABLE 3

| Leveler Y (mL/L) | Accelerator Amount in TBA Units |
|---|---|
| 0 | 19.8 |
| 0.5 | 12.2 |
| 1 | 9.9 |
| 2 | 8.2 |
| 4 | 7.1 |
| 6 | 6.4 |

From these data it can clearly be seen that the presence of the leveler has an affect on the determination of the accelerator by TBA analysis.

EXAMPLE 5

Figure 5:
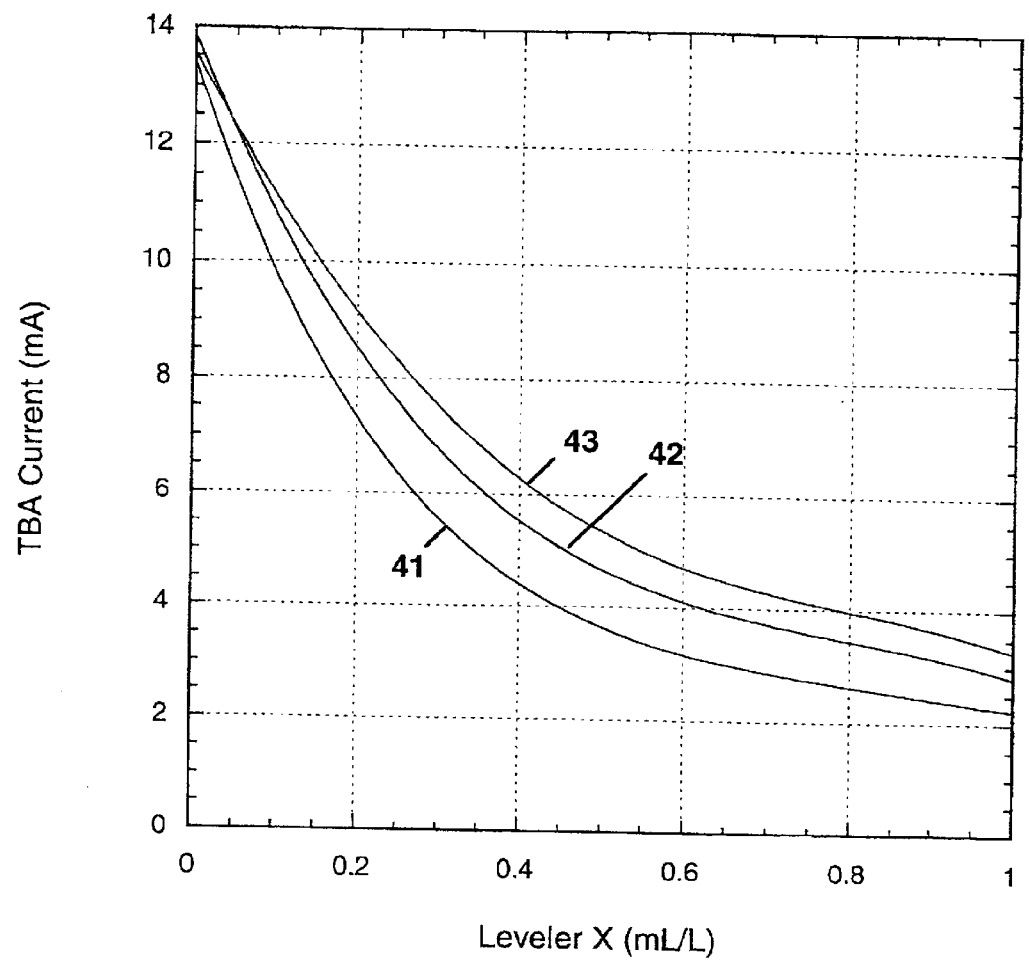
FIG. 5 is a curve showing the correlation showing correlation of the quantity of leveler X with TBA current for different concentrations of accelerator.

A series of copper electroplating baths was prepared according to Example 1 except that the amount of accelerator was 2, 3 or 4 mL/L and the amount of leveler X was up to 1 mL/L. Energy output (TBA current) versus leveler X concentration was formulated in accordance with the procedures of this invention. The TBA analysis was performed using the following cycle: +1.6 V for 5 seconds (forms oxide layer on working electrode), +0.5 V for 60 seconds (equilibration step), −0.242 V for 1 second (plating copper ions), and +0.2 V for 5 seconds (stripping step). FIG. 5 shows the changes in energy output in mA with leveler X concentration in mL/L for 2, 3 and 4 mL/L of accelerator, Lines 41, 42 and 43 respectively.

EXAMPLE 6

Figure 6:
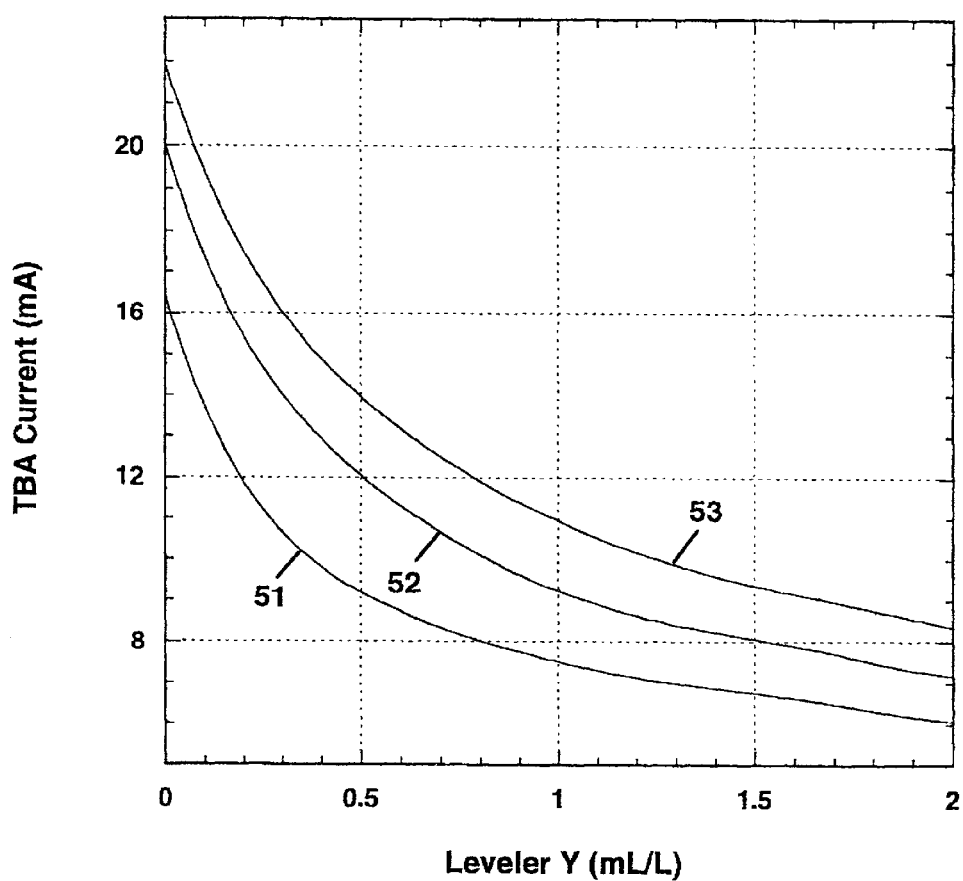
FIG. 6 is a curve showing the correlation showing correlation of the quantity of leveler Y with TBA current for different concentrations of accelerator.

A series of copper electroplating baths was prepared according to Example 1 except that the amount of accelerator was 1, 2 or 3 mL/L and a different leveler was used. Leveler Y was used in amounts up to 2 mL/L. Leveler Y is a reaction product of a heterocyclic amine with epichlorohydrin. Energy output (TBA current) versus leveler Y concentration curves were formulated in accordance with the procedures of this invention. FIG. 6 shows the changes in energy output in mA with leveler Y concentration in mL/L for 1, 2 and 3 mL/L of accelerator, Lines 51, 52 and 53 respectively.

EXAMPLE 7

A copper electroplating bath having unknown quantities of both accelerator and leveler is obtained. The quantity of accelerator is determined using CVS according to Example 1. The quantity of accelerator is used to determine the appropriate calibration curve (based on amount of accelerator present). The bath is then analyzed according to Example 5 and the energy output is determined. The energy output is then correlated with the quantity of leveler.

What is claimed is:

1. A method for determining the quantity of both brightener and leveler in an electroplating bath having an unknown quantity of brightener and leveler comprising the steps of:
    a) determining the amount of brightener in the electroplating bath having the unknown quantity of brightener and leveler by a method selected from cyclic voltammetric stripping and cyclic pulse voltammetric stripping;
    b) obtaining a plurality of plating baths where each bath has a known and different quantity of said brightener and leveler, but where the quantity of each in each bath differs from the quantity in the other baths;
    c) for each bath, providing a counter electrode, a cleaned working electrode and a reference electrode immersed in said bath, and carrying out a predetermined sequence of steps comprising:
        1. cleaning and oxidizing the surface of the working electrode at a fixed potential for a period of time;
        2. equilibrating said working electrode to absorb brightener according to a step selected from equilibrating without energy input for a time until the change in energy output with time is minimal and equilibrating for a set time at a fixed potential;
        3. plating metal ions on said working electrode with energy input for a time selected from a time sufficient to measure initial plating energy output and, a time sufficient to measure the change in energy output with time; and
        4. stripping at a potential and for a period of time sufficient to remove the metal ions plated in step 3;

d) for each bath, correlating the quantity of leveler with the energy output value obtained in step 3;

e) placing said electrodes in said electroplating bath having the unknown quantity of brightener and leveler and performing said predetermined sequence of steps;

f) choosing from said correlations in step d), a particular correlation for a bath containing substantially the amount of brightener determined in step a); and g) choosing from the particular correlation in step f), a quantity of leveler which corresponds to said energy outputs recorded for said electroplating bath having the unknown quantity of brightener and leveler.

2. The method of claim 1 wherein the electroplating bath is a copper electroplating bath.

3. The method of claim 1 wherein the working electrode is a platinum electrode.

4. The method of claim 1 wherein the electrode is a rotating disk electrode.

5. A method for determining the quantity of both brightener and leveler in an electroplating bath having an unknown quantity of both brightener and leveler comprising the steps of:

a) obtaining a plurality of plating baths, where each bath has a known and different quantity of said brightener and leveler, but where the quantity of each in each bath differs from the quantity in the other baths;

b) sweeping for each of said baths an inert, working electrode at a predetermined rate through a plurality of voltanimetric cycles until a condition of steady state is obtained, each of said voltammetric cycles including a metal plating range and a metal stripping range for each of said baths of said plurality of baths, each of said voltammetric cycles comprising sweeping of a voltage toward one polarity followed by a sweeping of said voltage toward a reverse of said one polarity to complete said cycle;

c) measuring the coulombs utilized during said metal stripping range of said cycle for each of said baths of said plurality of baths, whereby a correlation is obtained between the effective quantity of brightener and said coulombs utilized during said metal stripping range;

d) providing the electroplating bath having the unknown quantity of both brightener and leveler;

e) sweeping for said bath having the unknown quantity of both brightener and leveler an inert, working electrode at said predetermined rate through a plurality of voltammetric cycles until a condition of steady state is obtained, each of said voltammetric cycles including a metal plating range and a metal stripping range for said electroplating bath having the unknown quantity of both brightener and leveler, each of said voltammetric cycles comprising a sweeping of a voltage toward one polarity followed by a sweeping of said voltage toward a reverse of said one polarity to complete said cycle;

f) measuring the coulombs utilized during said metal stripping range of said cycle for said electroplating bath having the unknown quantity of both brightener and leveler;

g) choosing from said correlation a quantity of brightener which corresponds to said coulombs utilized for said electroplating bath having the unknown quantity of both brightener and leveler;

h) for each of said plurality of plating baths in step a), providing a counter electrode, a cleaned working electrode and a reference electrode immersed in said bath, and carrying out a predetermined sequence of steps comprising:

1. cleaning and oxidizing the surface of the working electrode at a fixed potential for a period of time;
 2. equilibrating said working electrode to absorb brightener according to a step selected from equilibrating without energy input for a time until the change in energy output with time is minimal and equilibrating for a set time at a fixed potential;
 3. plating metal ions on said working electrode with energy input for a time selected from a time sufficient to measure initial plating energy output and a time sufficient to measure the change in energy output with time; and
 4. stripping at a potential and for a period of time sufficient to remove the metal ions plated in step 3;

i) for each bath, correlating the quantity of leveler with the energy output value obtained in step 3;

j) placing said electrodes in said electroplating bath having the unknown quantity of both brightener and leveler and performing said predetermined sequence of steps;

k) choosing from said correlations in step i), a particular correlation for a bath containing substantially the amount of brightener determined in step g); and l) choosing from the particular correlation in step k), a quantity of leveler which corresponds to said energy outputs recorded for said electroplating bath having the unknown quantity of brightener and leveler.

6. The method of claim 5 wherein the electroplating bath is a copper electroplating bath.

7. The method of claim 5 wherein the working electrode is a platinum electrode.

8. The method of claim 5 wherein the electrode is a rotating disk electrode.

* * * * *